US010338013B1

(12) United States Patent
Brodie et al.

(10) Patent No.: US 10,338,013 B1
(45) Date of Patent: Jul. 2, 2019

(54) POSITION FEEDBACK FOR MULTI-BEAM PARTICLE DETECTOR

(71) Applicant: KLA-Tencor Corporation, Milpitas, CA (US)

(72) Inventors: Alan D. Brodie, Palo Alto, CA (US); Christopher Sears, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/879,611

(22) Filed: Jan. 25, 2018

(51) Int. Cl.
*G01N 23/22* (2018.01)
*H01J 37/10* (2006.01)
*G01N 23/2251* (2018.01)
*G01N 23/2255* (2018.01)

(52) U.S. Cl.
CPC ..... *G01N 23/2251* (2013.01); *G01N 23/2255* (2013.01); *G01N 2223/6116* (2013.01)

(58) Field of Classification Search
CPC .... H01J 37/244; H01J 37/10; H01J 37/36177; H01J 2237/24592; H01J 2237/2817; H01J 2237/103; H01J 2237/1501; H01J 2237/221; H01J 2237/28; G01N 2223/505; G01N 23/22
USPC ........ 250/307, 311, 397, 332; 315/149, 150; 378/19
See application file for complete search history.

(56) References Cited

U.S. PATENT DOCUMENTS

| | | | |
|---|---|---|---|
| 6,175,611 B1 * | 1/2001 | Melen | G01T 1/243 250/332 |
| 7,972,885 B1 * | 7/2011 | Dutta | B82Y 20/00 257/E21.007 |
| 9,153,413 B2 * | 10/2015 | Almogy | H01J 37/05 |
| 9,495,499 B2 * | 11/2016 | Platzgummer | G06F 17/5072 |
| 9,536,702 B2 * | 1/2017 | Lang | H01J 37/222 |
| 9,709,386 B1 * | 7/2017 | Nicolaides | G01B 11/0641 |
| 9,805,910 B1 * | 10/2017 | Trease | H01J 37/263 |
| 2005/0200291 A1 * | 9/2005 | Naugler, Jr. | G06F 3/0412 315/149 |
| 2007/0228274 A1 * | 10/2007 | Elyasaf | G01N 23/2251 250/306 |
| 2009/0114818 A1 * | 5/2009 | Casares | H01J 37/045 250/307 |
| 2013/0032729 A1 * | 2/2013 | Knippelmeyer | H01J 37/09 250/394 |
| 2013/0187046 A1 * | 7/2013 | Zeidler | B82Y 10/00 250/310 |

(Continued)

*Primary Examiner* — David A Vanore
(74) *Attorney, Agent, or Firm* — Suiter Swantz pc llo

(57) ABSTRACT

A multi-beam metrology system includes an illumination source configured to generate a beam array, an illumination sub-system to direct the beam array to a sample at an array of measurement locations, an imaging sub-system to image the array of measurement locations as an array of imaged spots in a detection plane, and a detection assembly to generate detection signal channels associated with each of the imaged spots. The detection assembly includes an array of detection elements configured to receive the imaged spots with separate detection elements, and one or more position detectors to measure positions of the imaged spots in the detection plane. The detection assembly further generates feedback signals for the imaging sub-system based on the measured positions of the imaged spots to adjust the positions of one or more of the imaged spots in the detection plane to maintain alignment of the array of detection elements.

31 Claims, 12 Drawing Sheets

(56) References Cited

U.S. PATENT DOCUMENTS

| | | | | |
|---|---|---|---|---|
| 2015/0001418 A1* | 1/2015 | Ido | ............... | H01J 37/3171 |
| | | | | 250/397 |
| 2015/0083911 A1* | 3/2015 | Zeidler | ............ | H01J 37/226 |
| | | | | 250/310 |
| 2015/0090879 A1* | 4/2015 | Zeidler | ............ | H01J 37/28 |
| | | | | 250/307 |
| 2015/0348738 A1* | 12/2015 | Zeidler | ............ | H01J 37/10 |
| | | | | 250/396 R |
| 2015/0357157 A1* | 12/2015 | Mueller | ............ | H01J 37/21 |
| | | | | 250/396 R |
| 2016/0247663 A1* | 8/2016 | Schubert | ............ | H01J 37/28 |
| 2017/0243715 A1* | 8/2017 | Ogasawara | ............ | H01J 37/20 |
| 2017/0278666 A1* | 9/2017 | Laske | ............ | H01J 37/10 |
| 2017/0287675 A1* | 10/2017 | Hegde | ............ | H01J 37/28 |
| 2018/0068825 A1* | 3/2018 | Brodie | ............ | H01L 22/00 |
| 2018/0136344 A1* | 5/2018 | Nelson | ............ | A61B 6/4233 |
| 2018/0158644 A1* | 6/2018 | Jiang | ............ | H01J 37/1474 |
| 2018/0166247 A1* | 6/2018 | Moore | ............ | H01J 37/02 |

\* cited by examiner

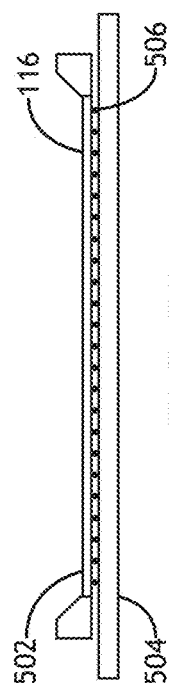
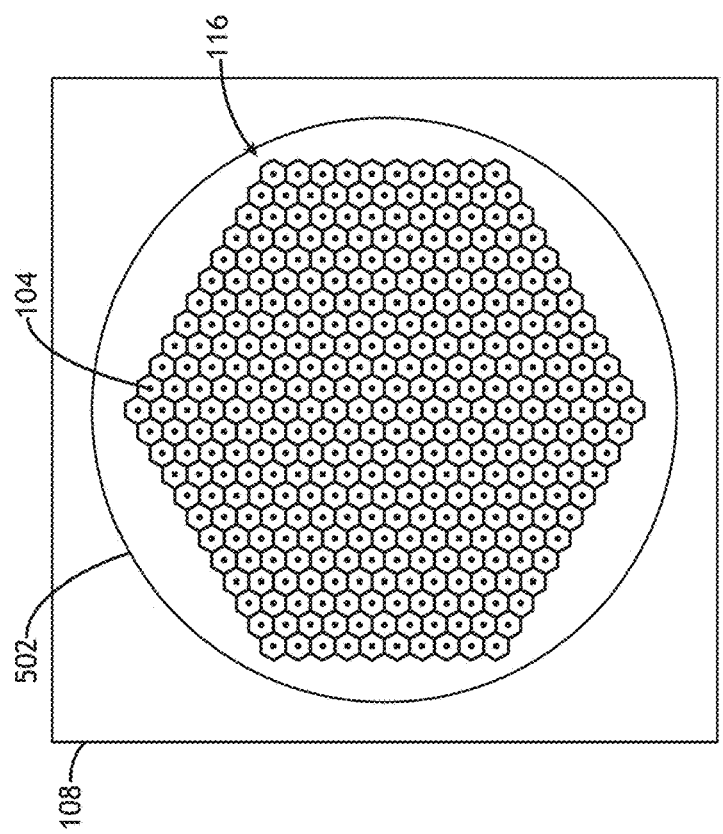

POSITION FEEDBACK FOR MULTI-BEAM PARTICLE DETECTOR

TECHNICAL FIELD

The present disclosure relates generally to particle beam detection and, more particularly, to position detection of multiple particle beams.

BACKGROUND

Inspection systems identify and classify defects on semiconductor wafers to generate a defect population on the sample. Further, inspection systems may identify defects on unprocessed wafers (e.g., prior to one or more fabrication steps) or at any time during sample fabrication. A given semiconductor wafer including one or more fabricated layers may include hundreds of chips, each chip containing thousands of components of interest, and each component of interest may have millions of instances on a given layer of a chip. As a result, inspection systems may generate vast numbers of data points (e.g., hundreds of billions of data points for some systems) on a given wafer. Further, the demand for ever-shrinking devices leads to increased demands on inspection systems, which may negatively impact the throughput. Therefore, it would be desirable to provide a system and method for curing shortcomings such as those identified above.

SUMMARY

A multi-beam metrology system is disclosed in accordance with one or more illustrative embodiments of the present disclosure. In one illustrative embodiment, the system includes an illumination source configured to generate a beam array. In another illustrative embodiment, the system includes an illumination sub-system configured to direct the beam array to a sample at an array of measurement locations. In another illustrative embodiment, the system includes an imaging sub-system configured to image the array of measurement locations as an array of imaged spots in a detection plane, the imaging sub-system further configured to adjust positions of one or more of the imaged spots in the detection plane. In another illustrative embodiment, the system includes a detection assembly configured to generate detection signal channels associated with each of the imaged spots. In one illustrative embodiment, the detection assembly includes an array of detection elements configured to receive the imaged spots with separate detection elements. In another illustrative embodiment, the detection assembly includes one or more position detectors configured to measure positions of the imaged spots in the detection plane. In another illustrative embodiment, the detection assembly generates feedback signals for the imaging sub-system based on the measured positions of the imaged spots to adjust the positions of one or more of the imaged spots in the detection plane to maintain alignment of the array of detection elements.

A detection assembly is disclosed in accordance with one or more illustrative embodiments of the present disclosure. In one illustrative embodiment, the detection assembly includes an array of detection elements configured to receive one or more imaged spots at a detection plane with separate detection elements. In another illustrative embodiment, the one or more imaged spots include radiation emanating from a sample in response to a beam array from a multi-beam illumination source and imaged to the detection plane by an imaging sub-system, of an imaging sub-system. In another illustrative embodiment, the detection assembly includes one or more position detectors configured to measure positions of the imaged spots in the detection plane. In another illustrative embodiment, the detection assembly generates feedback signals for the imaging sub-system based on the measured positions of the imaged spots in the detection plane to adjust the positions of one or more of the imaged spots in the detection plane to maintain alignment of the array of detection elements.

A method for detecting positions of multiple particle beams is disclosed in accordance with one or more illustrative embodiments of the present disclosure. In one illustrative embodiment, the method includes generating a particle beam array with an illumination source. In one illustrative embodiment, the method includes directing the particle beam array to an array of measurement locations on a sample with an illumination sub-system. In one illustrative embodiment, the method includes imaging the array of measurement locations to an array of imaged spots at a detection plane with an imaging sub-system. In another illustrative embodiment, the method includes receiving the imaged spots with separate detection elements of an array of detection elements. In another illustrative embodiment, the method includes measuring, with one or more position detectors, positions of the imaged spots at the detection plane. In another illustrative embodiment, the method includes generating feedback signals for the imaging sub-system based on the measured positions of the imaged spots to adjust the positions of the one or imaged spots in the detection plane to maintain alignment of the array of detection elements.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which:

FIG. 5A is a top view of a detection assembly including an array of detection elements, in accordance with one or more embodiments of the present disclosure.

FIG. 5B is a side view of a detection assembly including an array of PIN detection elements fabricated on a common substrate layer, in accordance with one or more embodiments of the present disclosure.

DETAILED DESCRIPTION

Figure 1:
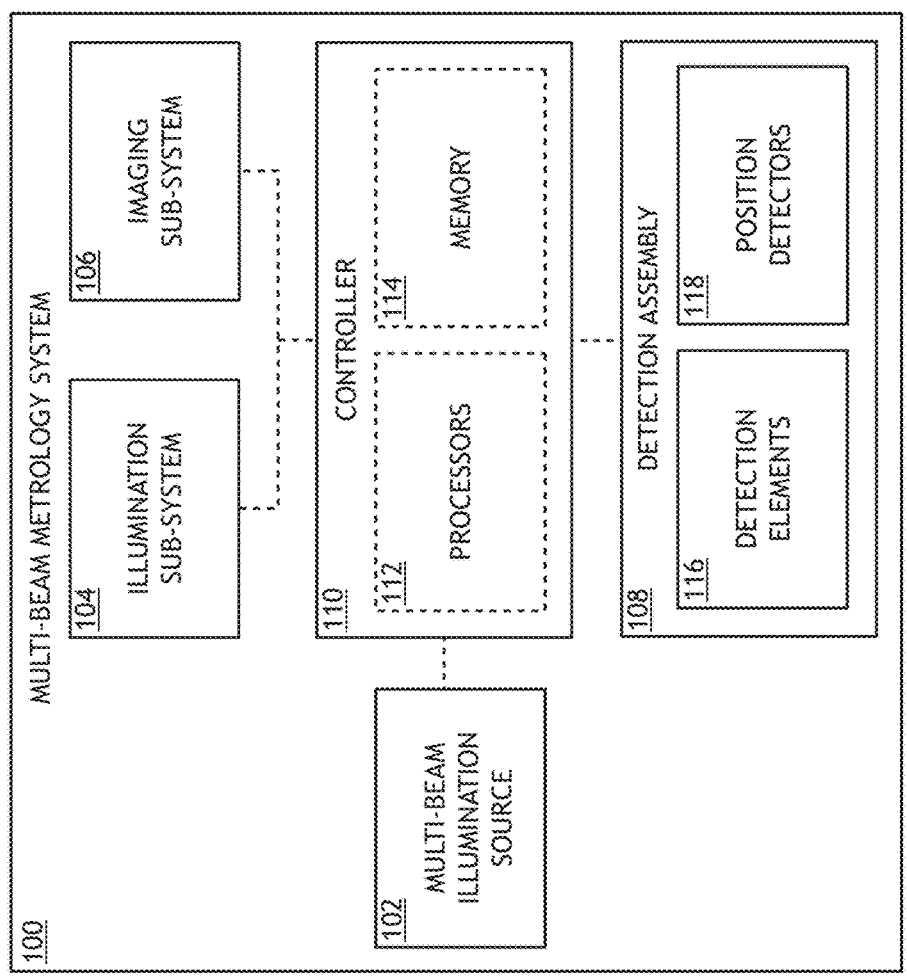
FIG. 1 is a conceptual view of a multi-beam inspection system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to a multi-beam inspection system including an illumination sub-system to direct a beam array to a sample at an array of measurement locations, an imaging sub-system to image the measurement locations as an array of imaged spots at a detection plane, and a detection assembly to generate detection signal channels associated with each of the imaged spots. In this regard, multiple portions of the sample may be interrogated in parallel (e.g., the array of measurement locations), which may provide increased throughput relative to a system without arrays of beams.

Sample inspection may generally be performed using any type of illumination beam known in the art such as, but not limited to, particle beams (e.g., electron beams, ion beams, or the like), or beams of electromagnetic radiation (e.g., X-rays, optical beams, or the like). For example, a particle beam inspection system may typically have a higher resolution, but a lower throughput, than an optical beam inspection system. Accordingly, inspection systems with different types of illumination beams may be utilized individually or in combination to take advantage of complementary advantages.

As used throughout the present disclosure, the term sample generally refers to any sample suitable for inspection. For example, a sample may include an unprocessed semiconductor or non-semiconductor material (e.g., a wafer, or the like). A semiconductor or non-semiconductor material may include, but is not limited to, monocrystalline silicon, gallium arsenide, and indium phosphide. By way of another example, a sample may include a semiconductor device at any stage of fabrication. For instance, a semiconductor device may be formed as one or more layers of patterned or unpatterned material. Such layers may include, but are not limited to, a resist, a dielectric material, a conductive material, and a semiconductive material. Many different types of such layers are known in the art, and the term sample as used herein is intended to encompass a sample on which all types of such layers may be formed. Many different types of devices may be formed on a sample, and the term sample as used herein is intended to encompass a sample on which any type of device known in the art is being fabricated. By way of another example, a sample may include one or more elements used in a fabrication process such as, but not limited to, a reticle or a photomask.

For example, a sample may include a plurality of dies, each having repeatable patterned features. Formation and processing of such layers of material may ultimately result in completed devices. Further, for the purposes of the present disclosure, the term sample and wafer should be interpreted as interchangeable. In addition, for the purposes of the present disclosure, the terms patterning device, mask, and reticle should be interpreted as interchangeable.

Additional embodiments of the present disclosure are directed to a detection assembly including an array of detection elements configured to receive each of the imaged spots with a separate detection element. For example, the array of detection elements may generate a separate detection channel associated with each of the imaged spots, which are in turn associated with each beam of the beam array. In this regard, an image of the sample may be formed by combining the detection channel signals associated with each of the imaged spots on the sample. Further, the sample and/or the beam array may be translated to build up a sample image of any arbitrary size.

Additional embodiments of the present disclosure are directed to a detection assembly including position detectors to measure positions of the imaged spots at the detection plane. In this regard, the positions of the imaged spots on the individual detection elements may be monitored.

The detector assembly may be configured in various ways to simultaneously image the sample and monitor the positions of each imaged spot in the detection plane. For example, the detector assembly may include an array of multi-pixel detection elements located at the detection plane to directly receive the imaged spots. Further, the one or more position detectors may include one or more pixels of the multi-pixel detection elements. The position of an imaged spot on a multi-pixel detection element may thus be determined based on the relative signal strengths of each pixel. By way of another example, the detector assembly may include a detector imaging system to provide a first image at the detection plane onto input faces of an optical fiber array coupled to detection elements and a second image (e.g., via a beamsplitter) to a position-monitoring camera. Such a configuration may be suitable for any type of illumination beam. For instance, the detector assembly for a particle beam inspection system may include a scintillator located at the detection plane to generate photons in response to absorbed secondary electrons from the sample associated with the imaged spots. The detector imaging system may then image the light generated by the scintillator onto the array of optical fibers as well as the position monitoring camera.

Additional embodiments of the present disclosure are directed to providing feedback signals to the imaging sub-system to adjust the positions of the imaged spots in the detection plane to maintain alignment of the array of detection elements based on the output of the position detectors. For example, the imaging sub-system may include one or more adjustable beam-control elements (e.g., focusing elements, aberration correcting elements, or the like) suitable for modifying the positions of one or more of the imaged spots at the detection plane.

It is recognized herein that accurate alignment of the array of imaged spots and the array of detection elements is essential not only for initial system alignment, but also for continued operation. For example, alignment of the array of imaged spots and the array of detection elements may reduce and/or minimize cross-talk between detection elements. By way of another example, the sensitivity of a detection element may vary as a function of position across an input face. For instance, in the case that the array of detection elements includes an array of optical fibers coupled to optical detectors, the relative positions of the imaged spots on the input faces of the fibers will strongly influence the coupling efficiency of light into the fibers.

It is further recognized herein that the positions of imaged spots in the detection plane may shift due to a variety of sample variations such as, but not limited to, variations of physical properties, electrical properties, chemical properties, or optical properties. For example, sample tilt may cause all imaged spots to shift in a common direction. By way of another example, charging effects in a particle beam inspection system may cause some imaged spots to shift relative to others leading to asymmetric distortions at the sample plane.

Additional embodiments of the present disclosure are directed to providing feedback signals to the imaging sub-system to compensate for measured deviations of the imaged spots at the detection plane. In this regard, the feedback signals may maintain alignment of the detector elements in response to variations on the sample.

Additional embodiments of the present disclosure are directed to utilizing the positions of the imaged spots as supplemental inspection data. In this regard, the positions of the imaged spots in the detection plane may provide diagnostic information about variations on the sample (e.g., sample tilt, a distribution of charging effects, or the like) that may supplement the image generated by the detection elements.

FIG. 1 is a conceptual view of a multi-beam inspection system 100, in accordance with one or more embodiments of the present disclosure. In one embodiment, the multi-beam inspection system 100 includes a multi-beam illumination source 102 to generate an array of illumination beams (e.g., a beam array, a beamlet array, or the like), an illumination sub-system 104 to illuminate a sample with the beam array at an array of measurement locations (e.g., located at an image plane of the illumination sub-system 104), an imaging sub-system 106 to image the array of measurement locations to a detection plane as an array of imaged spots, and a detection assembly 108 to receive the array of imaged spots at the detection plane and generate detection signal channels associated with each imaged spot. In this regard, the multi-beam inspection system 100 may simultaneously interrogate a sample with each illumination beam. In another embodiment, the multi-beam inspection system 100 includes a controller 110 including one or more processors 112 configured to execute program instructions maintained on a memory medium 114. In this regard, the one or more processors 112 of controller 110 may execute any of the various process steps described throughout the present disclosure.

The one or more processors 112 of a controller 110 may include any processing element known in the art. In this sense, the one or more processors 112 may include any microprocessor-type device configured to execute algorithms and/or instructions. In one embodiment, the one or more processors 112 may consist of a desktop computer, mainframe computer system, workstation, image computer, parallel processor, or any other computer system (e.g., networked computer) configured to execute a program configured to operate the multi-beam inspection system 100, as described throughout the present disclosure. It is further recognized that the term "processor" may be broadly defined to encompass any device having one or more processing elements, which execute program instructions from a non-transitory memory medium 114.

The memory medium 114 may include any storage medium known in the art suitable for storing program instructions executable by the associated one or more processors 112. For example, the memory medium 114 may include a non-transitory memory medium. By way of another example, the memory medium 114 may include, but is not limited to, a read-only memory ROM), a random access memory (RAM), a magnetic or optical memory device (e.g., disk), a magnetic tape, a solid state drive, and the like. It is further noted that memory medium 114 may be housed in a common controller housing with the one or more processors 112. In one embodiment, the memory medium 114 may be located remotely with respect to the physical location of the one or more processors 112 and controller 110. For instance, the one or more processors 112 of controller 110 may access a remote memory (e.g., server), accessible through a network (e.g., internet, intranet and the like). Therefore, the above description should not be interpreted as a limitation on the present invention but merely an illustration.

The imaging sub-system 106 may collect any type of particles and/or radiation emanating from the sample from the array of measurement locations to generate the array of imaged spots at the detection plane. For example, in response to the incident illumination beams, the sample may radiate electromagnetic radiation (e.g., X-rays, optical radiation, or the like) and/or particles (e.g., secondary electrons, backscattered electrons, ions, neutral particles, or the like). Accordingly the imaged spots may include electromagnetic radiation and/or particles collected by the imaging sub-system 106.

In another embodiment, the detection assembly 108 includes an array of detection elements 116. For example, the detection assembly 108 may receive each imaged spot (e.g., the electromagnetic radiation and/or particles emanating from the sample in response to the illumination beams) with a separate detection element 116. In this regard, the detection assembly 108 may generate a separate data signal (e.g., a detection channel signal) associated with each measurement location on the sample illuminated by an illumination beam. Further the controller 110 may receive the detection channel signals from the detection elements 116.

In another embodiment, the detection assembly 108 includes one or more position detectors 118 to measure the positions of the imaged spots at the detection plane. The positions of the imaged spots at the detection plane may thus be representative of the positions of the alignment of imaged spots on the detection elements 116. Further, the controller 110 may receive position signals from the position detectors 118.

In another embodiment, the imaging sub-system 106 includes one or more adjustable beam control elements suitable for manipulating the positions of one or more illumination beams of the beam array at the detection plane. Accordingly, the controller 110 may generate feedback signals based on the position signals from the position detectors 118 and provide the feedback signals to the imaging sub-system 106. In this regard, the imaging sub-system 106 may continually adjust the positions of the imaged spots in the detection plane to maintain alignment of the detection elements 116.

Figure 2:
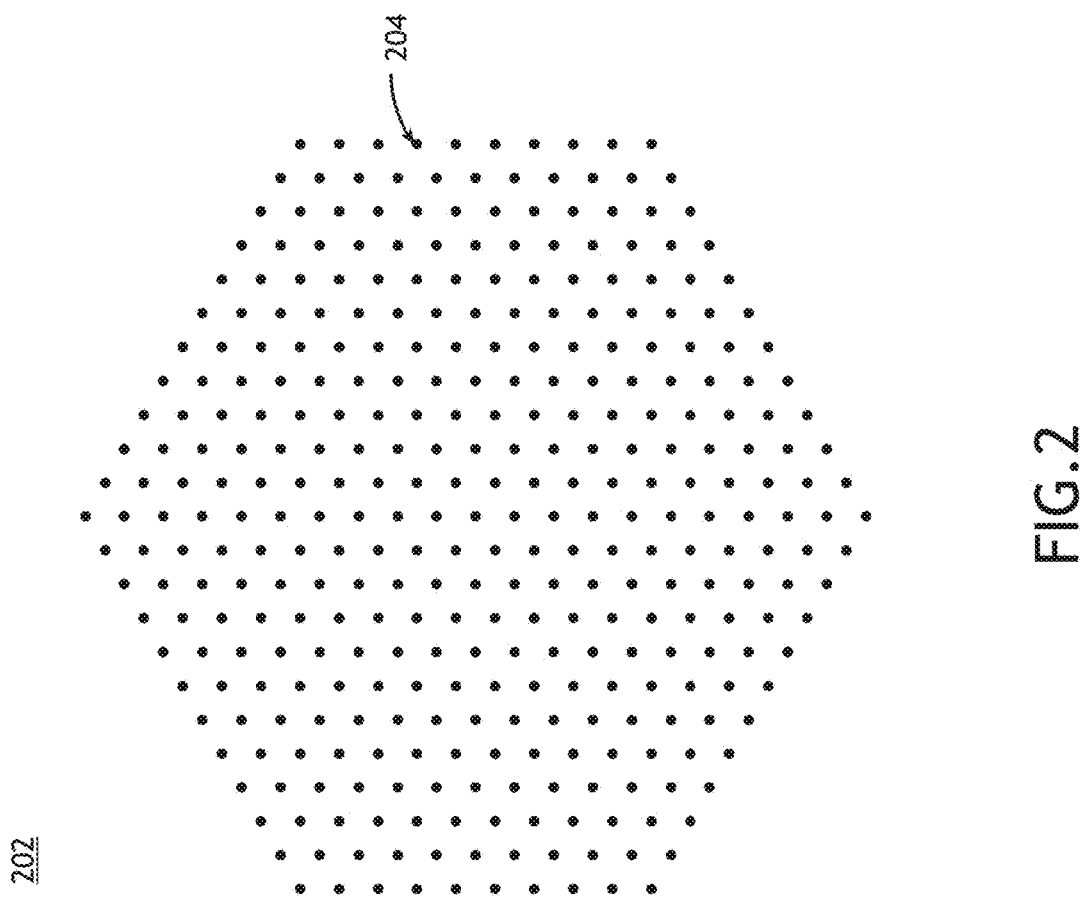
FIG. 2 is a plan view of a detection plane including a 2D array of imaged spots, in accordance with one or more embodiments of the present disclosure.
Figure 3:
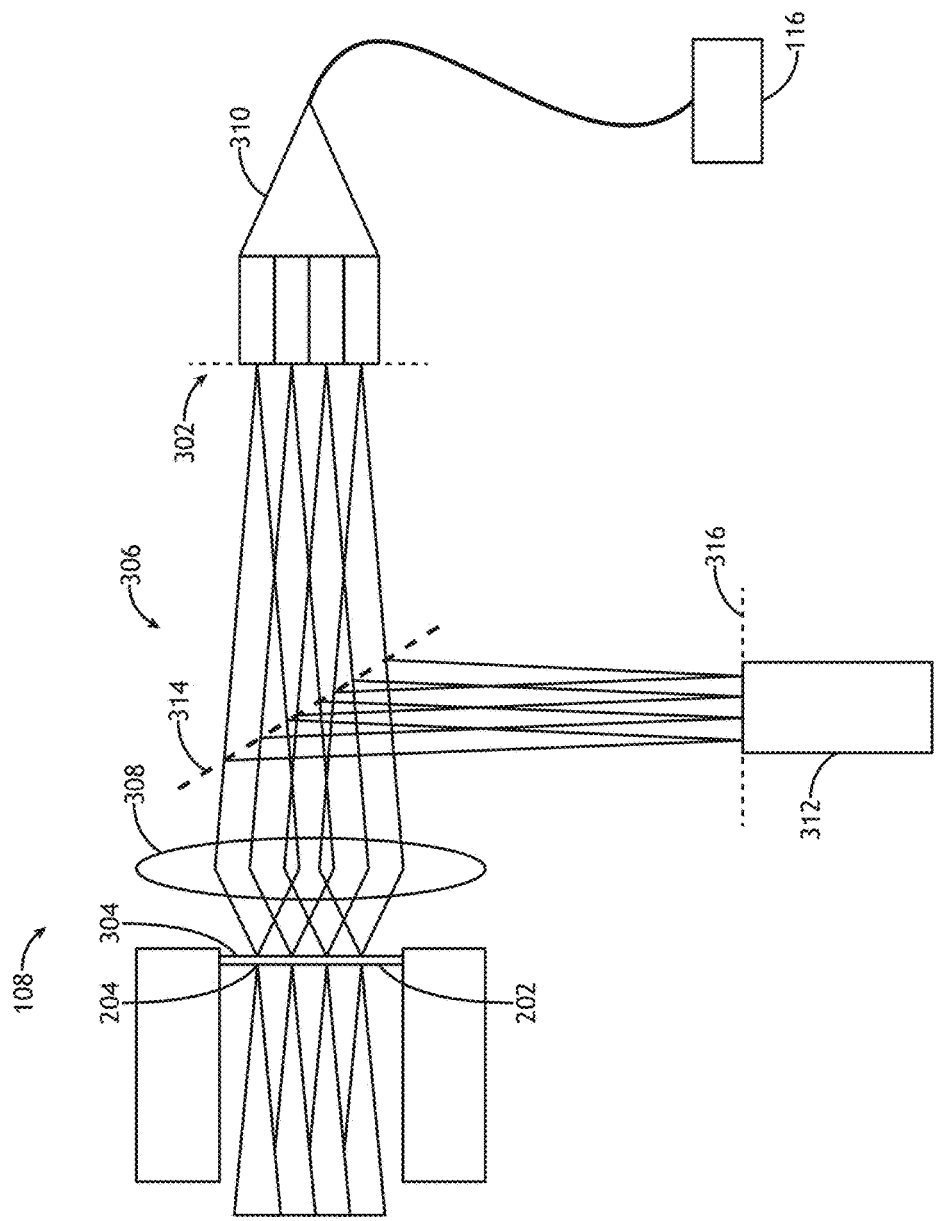
FIG. 3 is a conceptual view of a detection assembly in which the array of imaged spots at a detection plane is reimaged as a secondary image to a secondary detection plane, in accordance with one or more embodiments of the present disclosure.
Figure 4:
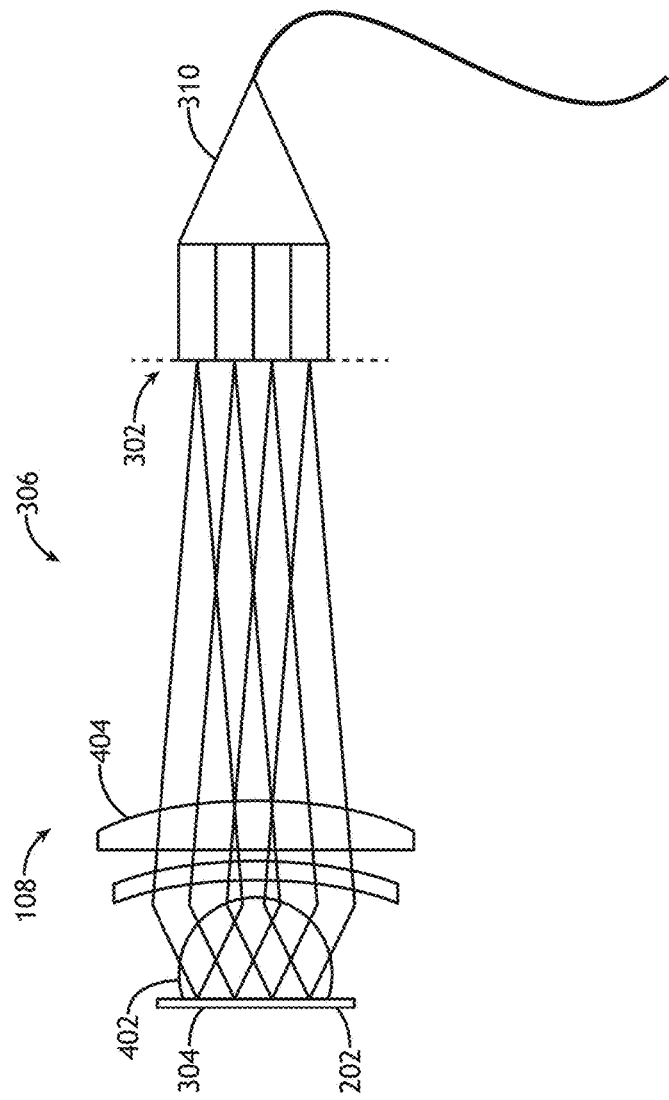
FIG. 4 is a conceptual view of a portion of a detection assembly including a solid immersion lens, in accordance with one or more embodiments of the present disclosure.

Referring now to FIGS. 2-4, embodiments of the detection assembly 108 for simultaneously generating detection signal channels for an array of imaged spots at a detection plane and monitoring the positions of the array of imaged spots at the detection plane are described.

FIG. 2 is a plan view of a detection plane 202 including a 2D array of imaged spots 204, in accordance with one or more embodiments of the present disclosure. As described previously herein, the imaged spots 204 may include particles and/or electromagnetic radiation emanating from a sample generated in response to an array of illumination beams. It is to be understood that number and distribution of the imaged spots 204 illustrated in FIG. 2 is provided solely for illustrative purposes and should not be interpreted as limiting. The detection assembly 108 may be configured to generate detection channel signals and determine positions of imaged spots 204 in any distribution known in the art.

FIG. 3 is a conceptual view of a detection assembly 108 in which the array of imaged spots 204 at a detection plane 202 is reimaged as a secondary image to a secondary detection plane 302, in accordance with one or more embodiments of the present disclosure. In one embodiment, the detection assembly 108 includes a scintillator 304 located at the detection plane 202 to absorb particles emanating from the sample and subsequently emit electromagnetic radiation (e.g., light). The scintillator 304 may include any type of scintillator known in the art suitable for generating light in response to absorbed particles. For example, the scintillator 304 may, but is not required to, include emit light a fluorescent material through fluorescence in response to the absorption of particles emitted by the camera 312 and captured by the imaging sub-system 106. Accordingly, the scintillator 304 may include any type of such fluorescent material including, but not limited to, organic or inorganic crystals or liquids. In one embodiment, the scintillator 304 includes a plastic scintillator including a polymer matrix that itself generates fluorescence in response to absorbed particles or includes fluorophores suspended within the polymer matrix.

In another embodiment, the scintillator 304 absorbs particles generated from a sample associated with the imaged spots 204 and subsequently emits light with visible wavelengths. In one instance, the scintillator 304 emits light with an approximately 20 nanometer bandwidth centered at approximately 400 nanometers.

In another embodiment, the scintillator 304 is selected to provide a rapid fluorescent decay time of the scintillator 304 to facilitate fast scanning of the sample and high throughput detection. For example, the fluorescent decay time of the scintillator 304 may be less than approximately 20 nanoseconds. By way of another example, the fluorescent decay time of the scintillator 304 may be less than approximately 10 nanoseconds. By way of another example, the fluorescent decay time of the scintillator 304 may be less than approximately 5 nanoseconds.

Further, the intensity of the light generated by the scintillator 304 may be proportional to the absorbed energy from the particles making up the imaged spots 204. In this regard, detection of the optical image at the secondary detection plane 302 may provide substantially the same information about the sample as detection of the imaged spots 204 including particles at the detection plane 202.

In another embodiment, the detection assembly 108 includes a detector imaging sub-system 306 to image light generated by the scintillator 304 in response to the imaged spots 204 to the secondary detection plane 302 as a secondary image. The detector imaging sub-system 306 may include any number of optical elements to capture light from the scintillator 304 and generate the secondary image at the secondary detection plane 302. For example, as illustrated in FIG. 3, the detector imaging sub-system 306 may include one or more detector lenses 308. In one instance, a detector lens 308 may include a high numerical aperture (high NA) lens (e.g., an objective lens, or the like).

In another embodiment, a detector imaging sub-system 306 includes a solid immersion lens (SIL) placed in contact with the scintillator 304 (or a substrate material in contact with the scintillator 304). For example, a SIL may include, but is not limited to a hemispherical lens or a truncated spherical lens (e.g., a Weierstrauss SIL or a superhemispherical SIL). FIG. 4 is a conceptual view of a portion of the detection assembly 108 including a solid immersion lens, in accordance with one or more embodiments of the present disclosure. In one embodiment, the detector imaging sub-system 306 includes a Weierstrauss SIL 402 in contact with the scintillator 304. The SIL 402 may provide a high NA for efficient collection of light from the scintillator 304. Further, the refractive index of the SIL 402 may be selected to, but is not required to be selected to, be similar to the refractive index of the scintillator 304 to limit refraction at the interface between the scintillator 304 and the SIL 402. In another embodiment, the detector imaging sub-system 306 includes one or more additional detector lenses 404 to collect light captured by the SIL 402 and generate the image of the detection plane 202 at the secondary detection plane 302.

In one embodiment, the detection assembly 108 includes an array of optical fibers 310 (e.g., a fiber bundle) positioned with input faces at the secondary detection plane 302. In this regard, the detector imaging sub-system 306 may couple light from the scintillator 304 associated with the imaged spots 204 into the optical fibers 310. For example, the spatial distribution of the optical fibers 310 may correspond to a scaled version of the distribution of illumination beams within the beam array. In this regard, the light associated with each imaged spot 204 may be coupled into a different optical fiber 310.

In another embodiment, the detector imaging sub-system 306 magnifies the detection plane 202 such that the secondary images of the imaged spots 204 match the core diameter of the optical fibers 310 to provide efficient coupling of light into the optical fibers 310. Further, it may be the case that the imaging sub-system 106 provides additional magnification of the sample when generating the imaged spots 204 at the detection plane 202. Accordingly, the size of the secondary image on the secondary detection plane 302 may include the combined magnification of the illumination sub-system 104 and the detector imaging sub-system 306 stages.

The optical fibers 310 may include any type of optical fibers with any core size available in the art. In one embodiment, the optical fibers 310 include multimode optical fibers. Cores of multimode optical fibers may typically range from approximately 200 micrometers to 1,600 micrometers. In one instance, an array of multimode optical fibers 310 having a 400 micrometer core diameter may require approximately 35λ total magnification to image an illuminated spot on the sample onto a core of an optical fiber 310 for efficient coupling. Accordingly, the required 35× magnification can be split between the imaging sub-system 106 and the detector imaging sub-system 306. For example, the spot imaging sub-system 106 may provide, but is not required to provide, approximately 3.5× magnification such that the detector imaging sub-system 306 may provide 10× magnification.

In another embodiment, the array of detection elements 116 within the detection assembly 108 may be coupled to output faces of the optical fibers 310 to detect light coupled into the optical fibers 310. Accordingly, the detection assembly 108 may provide separate detection signal channels for light associated with each imaged spot 204 (associated with portions of the sample illuminated by each illumination beam).

The detection elements 116 may include any type of optical detectors known in the art suitable for detecting light generated by the scintillator 304. In one embodiment, the detection elements 116 include light-sensitive diodes. In another embodiment, the detection assembly 108 includes one or more amplifiers to increase the detection sensitivity. For example, the detection elements 116 may include, but are not required to include, avalanche photodiodes (APDs) providing internal analog gain. By way of another example, the detection assembly 108 may include electronic amplifiers to amplify the electronic detection signals provided by the detection elements 116.

It is recognized herein that the output faces of the optical fibers 310 may be arranged in any distribution and need not correspond to the distribution of the input faces. For example, the output faces of the optical fibers 310 may be separated from each other to provide physical space required for the detection elements 116.

In another embodiment, a least a portion of the multi-beam inspection system 100 is contained within a vacuum chamber. Further, the detection assembly 108 may be located either within the chamber, outside of the chamber, or partially inside the chamber. For example, the scintillator 304 may be integrated with a window of the vacuum chamber such that at least a portion of the detection assembly 108 may be located outside of the vacuum chamber. In one instance, the scintillator 304 is mounted inside a window flange in the place of or alongside a transparent window material. In this regard, one face of the scintillator 304 may face the vacuum chamber and be exposed to particles emanating from the sample associated with the imaged spots 204. Further, the light emitted by scintillator 304 may propagate outside the chamber for collection with the detector imaging sub-system 306.

In another instance, a SIL 402 may be directly mounted to the vacuum chamber window (e.g., the scintillator 304 or a transparent window material proximate to the scintillator 304) with optical grease to collect the light from the scintillator 304. Further, the additional detector lenses 404 of the detector imaging sub-system 306 may be mounted to the SIL 402 in a fixed position to generate the secondary image of the imaged spots 204.

In another embodiment, the array of detection elements 116 is located directly at the secondary detection plane 302 (e.g., in place of the array of optical fibers 310 illustrated in FIGS. 3 and 4). For example, the spatial distribution of the array of detection elements 116 may correspond to a scaled version of the distribution of illumination beams within the beam array such that the light associated with each imaged spot 204 may be directed to a separate detection element 116.

In another embodiment, as illustrated in FIG. 3, the one or more position detectors 118 of the detection assembly 108 may include a camera 312 positioned to receive conjugate image of the secondary detection plane 302. For example, the detector imaging sub-system 306 may include a beamsplitter 314 positioned such that the detector imaging sub-system 306 may generate conjugate images at the secondary detection plane 302 and a camera detection plane 316. Further, the inclusion of the beamsplitter 314 in the context of FIG. 3 is provided solely for illustrative purposes and should not be interpreted as limiting. Rather, the beamsplitter 314 may be included in any design of the detector imaging sub-system 306. In one instance, a beamsplitter 314 may be incorporated into the detector imaging sub-system 306 illustrated in FIG. 4. In this regard, the beamsplitter 314 may generate conjugate images at the secondary image plane and a camera detection plane 316 based on light collected by a SIL 402.

In another embodiment, the camera 312 generates position data for each of the imaged spots 204 in the detection plane. For example, the position data may derived from the pixel locations on the camera 312 receiving light from the scintillator 304 associated with each of the imaged spots 204. Further, the position data may track deviations of the positions of each of the imaged spots 204 in response to variations on the sample.

In another embodiment, position data generated by the camera 312 may be calibrated to a desired alignment of the detection elements 116 with respect to the imaged spots 204. For example, calibration may include determining nominal positions of the secondary images of the imaged spots 204 on the camera 312 that correspond to an alignment of the secondary images of the imaged spots 204 with the cores of the optical fibers 310. Accordingly, deviations of the positions of the imaged spots 204 measured by the camera may indicate misalignments of the optical fibers 310 and thus reduced signal on the detection elements 116 at the output faces of the optical fibers 310.

The camera 312 may include any type of measurement detector suitable for detecting light emitted from the scintillator 304. For example, the camera may include, but is not limited to, a charge-coupled device (CCD) or a complementary metal-oxide semiconductor (CMOS) device.

Referring now to FIGS. 5A through 6B, embodiments of a detection assembly 108 including a multi-pixel array of detection elements 116 for simultaneously measuring the intensities and positions of the imaged spots 204 are described. In this regard, the array of detection elements 116 may be positioned at the detection plane 202 and may directly detect the particles and/or electromagnetic radiation emanating from the sample associated with the imaged spots 204.

FIG. 5A is a top view of a detection assembly 108 including an array of detection elements 116, in accordance with one or more embodiments of the present disclosure. In one embodiment, the spatial distribution of the detection elements 116 may correspond to a scaled version of the distribution of illumination beams. Accordingly, each imaged spot 204 may be received by a separate detection element 116. Further, the dots in FIG. 5A indicate the nominal positions of the imaged spots 204 on the detection elements 116.

The detection elements 116 of FIG. 5A may include any type of detectors known in the art suitable for detecting particles and/or electromagnetic radiation emanating from the sample. In one embodiment, the detection elements 116 include diodes sensitive to electrons (e.g., secondary electrons and/or backscattered electrons). For example, the detection elements 116 may include PIN diodes. It is noted that avalanche gain (e.g., such as generated in APDs) may not be necessary and may, in some applications, induce excessive heating and/or excessive gain.

The detection elements 116 may further be fabricated and packaged using various techniques. FIG. 5B is a side view of a detection assembly 108 including an array of PIN detection elements 116 fabricated on a common substrate layer 502, in accordance with one or more embodiments of the present disclosure. In one embodiment, each detection element 116 includes at least one separate bond pad such that each detection element 116 may generate a separate detection signal channel. In another embodiment, as illustrated in FIG. 5B, the bond pads of the detection elements 116 may be connected to an external substrate 504 by filled vias 506 through the common substrate layer 502 such the detection signal channels may be connected to additional circuitry (e.g., to one or more amplifies, the controller 110, or the like). Further, the common substrate layer 502 may be, but is not required to be, back-thinned to provide both mechanical stability and short connections to the external substrate 504 for high-speed performance.

In another embodiment, the detection assembly 108 includes position detectors 118 integrated with each detection element 116 to determine the positions of the imaged spots 204 on the detection elements 116. For example, each detection element 116 may include two or more pixels. In this regard, the relative position of an imaged spot 204 on a detection element 116 may be determined based on the relative energy absorbed by the pixels with respect to the total energy absorbed by the detection element 116.

Figure 6B:
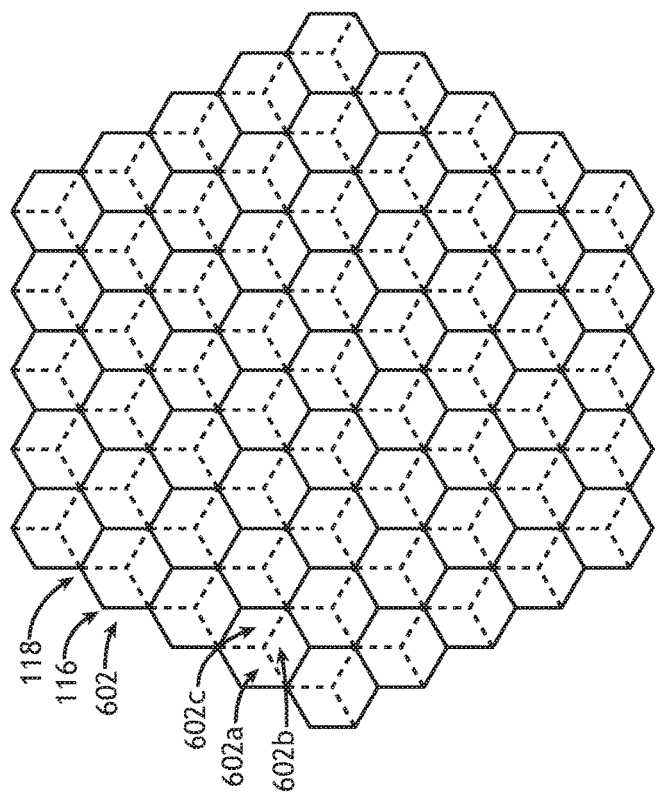
FIG. 6B is a top view of an array of detection elements in which each individual detection element includes three pixels operating as position detectors, in accordance with one or more embodiments of the present disclosure.
Figure 6A:
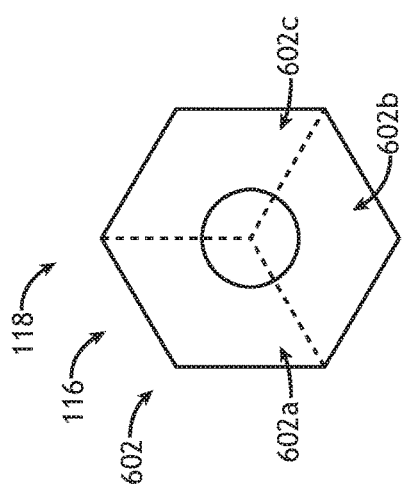
FIG. 6A is a conceptual view of a detection element including three pixels for position detection, in accordance with one or more embodiments of the present disclosure.

FIG. 6A is a conceptual view of a detection element 116 including three pixels 602 for position detection, in accordance with one or more embodiments of the present disclosure. In one embodiment, the detection element 116 includes a first pixel 602a, a second pixel 602b, and a third pixel 602c arranged such that the energy associated with a circular imaged spot 204 nominally centered on the detection element 116 will be equally divided between the three pixels 602a,b,c. However, deviations of the imaged spot 204 from the nominal position will result in unequal distribution of energy absorbed by the three pixels 602a,b,c. Accordingly, position data including the magnitude and direction of a deviation of the imaged spot 204 from the nominal position may be calculated given a known energy distribution of the imaged spot 204.

In another embodiment, each pixel 602 (e.g., pixels 602a,b,c of FIG. 6A) of the detection elements 116 may have a separate electrical connection to the external substrate 504 such that the absorbed energy of all pixels 602 may be separately accessed for the calculation of position data.

FIG. 6B is a top view of an array of detection elements 116 in which each individual detection element 116 includes three pixels 602 operating as position detectors 118, in accordance with one or more embodiments of the present disclosure. In this regard, the positions of each imaged spot 204 with respect to the detection elements 116 may be determined.

It is to be understood that the description of detection elements 116 having three pixels 602 provided in FIGS. 6A and 6B, along with the associated descriptions, are provided solely for illustrative purposes and should not be interpreted as limiting. The detection elements 116 of a detection assembly 108 may include any number of pixels for the generation of position data for incident imaged spots 204. It is recognized herein that the number and distribution of pixels 602 may influence the accuracy with which position data may be generated. For example, a detection element 116 including two pixels oriented symmetrically may determine position data along a single direction. By way of another example, a detection element 116 including four quadrants of the active area of the detection element 116 may determine position data based on the relative energy absorbed in each quadrant. Additionally, pixels 602 may be arranged in any geometry such as, but not limited to, an annular geometry.

In another embodiment, position signals including the positions of the imaged spots 204 in the detection plane 202 may be utilized as feedback signals to the imaging sub-system 106 to maintain alignment of the detection elements 116. For example, the imaging sub-system 106 may include one or more adjustable elements suitable for adjusting the positions of one or more of the imaged spots 204 in the detection plane 202 such as, but not limited to, adjustable focusing elements or aberration correcting elements.

Feedback signals including positions of the imaged spots 204 in the detection plane 202 may be utilized for a variety of purposes during the operation of a multi-beam inspection system 100. In one embodiment, the feedback signals are utilized to align the detection assembly 108 prior to runtime. In another embodiment, feedback signals are utilized to maintain alignment of the detection assembly 108 during runtime. For example, variations of the sample such as, but not limited to, physical, chemical, mechanical, or optical properties may lead to misalignments of one or more imaged spots 204 with respect to the detection elements 116. Accordingly, the feedback signals may provide a means to mitigate the misalignments.

FIGS. 7A through 9B illustrate several examples of sample variations and the impacts on the alignment of the detection elements 116.

Figure 7B:
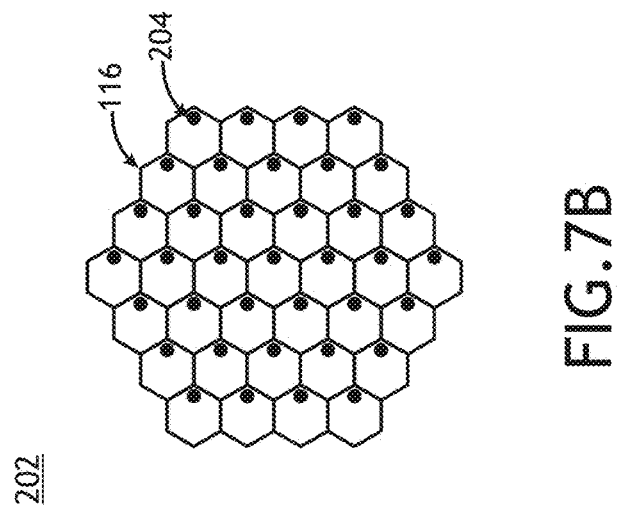
FIG. 7B is a conceptual top view of the detection plane in response to a tilted sample, in accordance with one or more embodiments of the present disclosure.
Figure 7A:
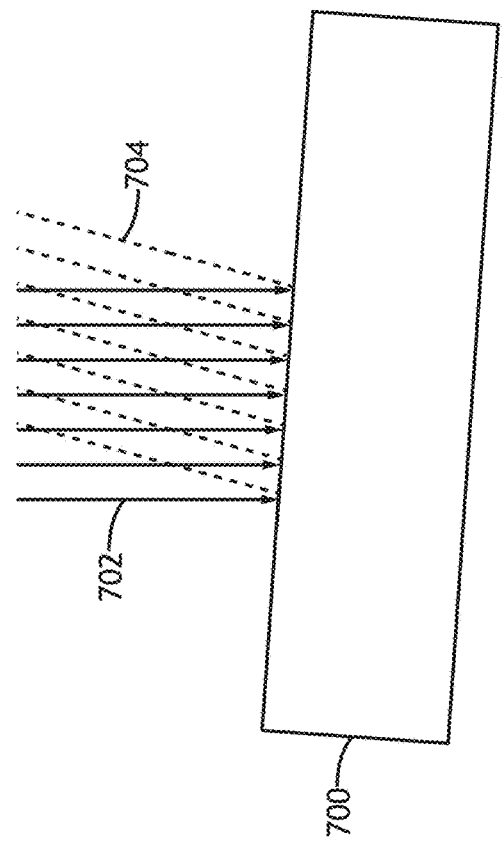
FIG. 7A is a conceptual side view of a tilted sample illustrating incident illumination beams (solid arrows) and resultant particles (dashed arrows) emanating from the sample, in accordance with one or more embodiments of the present disclosure.

FIG. 7A is a conceptual side view of a tilted sample 700 illustrating incident illumination beams 702 (solid arrows) and resultant particles 704 (dashed arrows) emanating from the sample 700, in accordance with one or more embodiments of the present disclosure. A tilted sample 700 will induce a uniform mismatch between the locations at which the array of illumination beams 702 impinge on the sample 700 and the array of measurement locations imaged by the imaging sub-system 106 along the direction of the tilt. FIG. 7B is a conceptual top view of the detection plane 202 in response to a tilted sample 700, in accordance with one or more embodiments of the present disclosure. In FIG. 7B, the imaged spots 204 are uniformly deflected from nominal positions on each of the detection elements 116. Accordingly, feedback signals generated by the position data may direct the imaging sub-system 106 to uniformly deflect (e.g., with a deflector) the imaged spots 204.

Figure 8B:
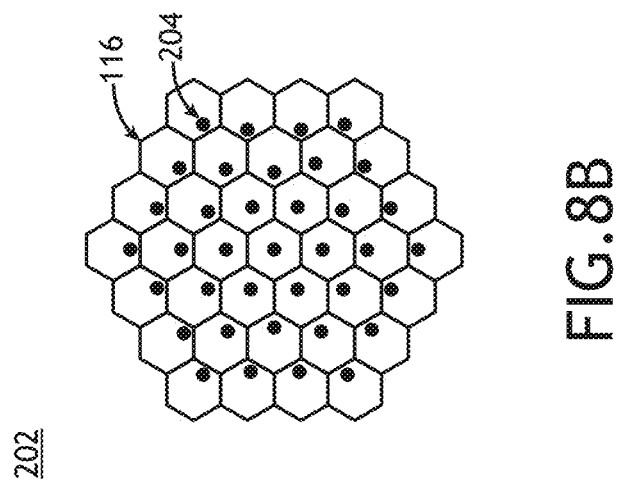
FIG. 8B is a conceptual top view of the detection plane in response to uniform sample charging, in accordance with one or more embodiments of the present disclosure.
Figure 8A:
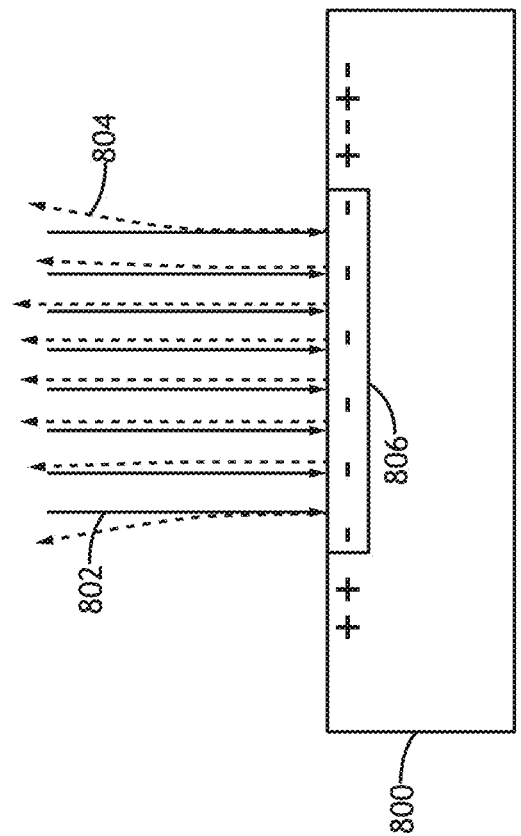
FIG. 8A is a conceptual side view of a sample exhibiting uniform charging in response to incident illumination beams and resultant particles emanating from the surface, in accordance with one or more embodiments of the present disclosure.

FIG. 8A is a conceptual side view of a sample 800 exhibiting uniform charging in response to incident illumination beams 802 (solid arrows) and resultant particles 804 (dashed arrows) emanating from the surface, in accordance with one or more embodiments of the present disclosure. For example, insulating structures and/or structures that are not connected to a ground source may develop a charge (e.g., a positive charge or a negative charge) in a region 806 in response to depletion of particles (e.g., secondary electrons, ions, or the like) induced by the beam array. Accordingly, the induced charge may deflect the trajectories of secondary electrons and thus the positions of the imaged spots 204 in the detection plane 202. FIG. 8B is a conceptual top view of the detection plane 202 in response to uniform sample charging, in accordance with one or more embodiments of the present disclosure. In FIG. 8B, the imaged spots 204 are non-uniformly, but symmetrically, deflected from nominal positions on each of the detection elements 116. For example, the uniform charging effects may induce lensing and higher-order aberration effects that cause the imaged spots 204 near the edges of the beam array to deflect with respect to those near the center. Accordingly, feedback signals generated by the position data may direct the imaging sub-system 106 to mitigate the lensing effect through focal adjustments and/or aberration corrections.

Figure 9B:
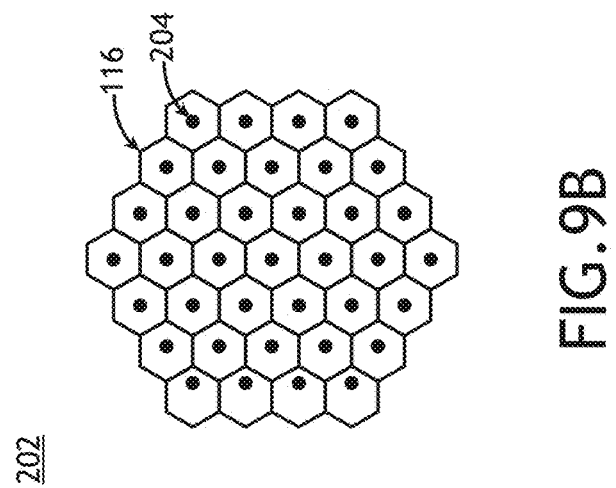
FIG. 9B is a conceptual top view of the detection plane in response to non-uniform sample charging, in accordance with one or more embodiments of the present disclosure.
Figure 9A:
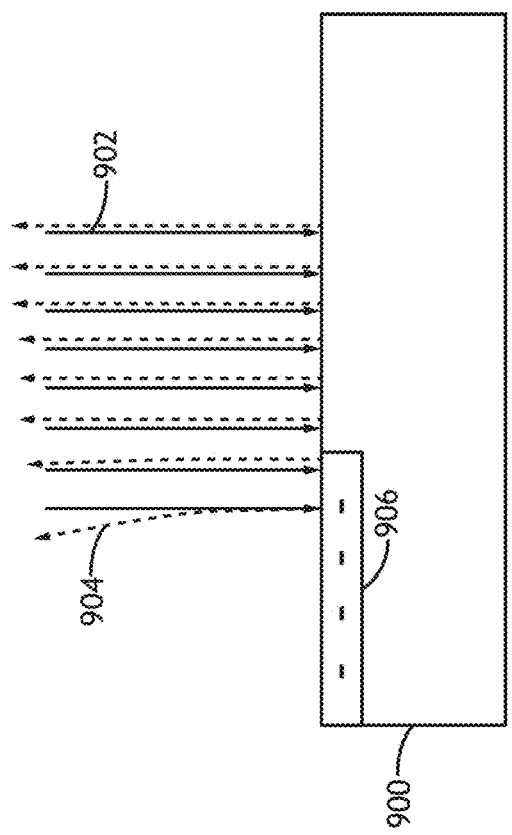
FIG. 9A is a conceptual side view of a sample exhibiting non-uniform charging, in accordance with one or more embodiments of the present disclosure.

FIG. 9A is a conceptual side view of a sample 900 exhibiting non-uniform charging in response to incident illumination beams 902 (solid arrows) and resultant particles 904 (dashed arrows) emanating from the surface, in accordance with one or more embodiments of the present disclosure. For example, variations in sample properties and/or the presence of patterned features may induce non-uniform charging effects (e.g., in region 906) that may non-uniformly deflect the trajectories of some imaged spots 204 with respect to others. FIG. 9B is a conceptual top view of the detection plane 202 in response to non-uniform sample charging, in accordance with one or more embodiments of the present disclosure. In FIG. 9B, the imaged spots 204 are non-uniformly and asymmetrically deflected from nominal positions on each of the detection elements 116. Accordingly, feedback signals generated by the position data may direct the imaging sub-system 106 to mitigate the lensing effect through asymmetric aberration corrections and/or deflections of some of the imaged spots 204.

It is to be understood that the examples of sample-induced misalignments and associated feedback corrections illustrated in FIGS. 7A through 9B are provided solely for illustrative purposes and should not be interpreted as limiting. It is recognized herein that misalignment of the detection assembly 108 may be induced by a complex variety of factors including sample-induced effects, beam drift, and the like. Further, it may be the case that feedback signals based on position data from the position detectors 118 may partially, rather than completely, mitigate the misalignment.

In another embodiment, position data of the imaged spots 204 generated by the position detectors 118 is used to supplement the intensity of the imaged spots 204 captured by the detection elements 116. For example, observed deflections of one or more imaged spots 204 may itself serve as diagnostic information relevant to the inspection of a sample. For example, as described previously herein and illustrated in FIGS. 8A through 9B, the relative positions of the imaged spots 204 in the detection plane 202 may be indicative of charging effects due to known structures as well as aberrant structures (e.g., defects).

Referring again to FIG. 1, the detection assembly 108 may be utilized in combination with any type of multi-beam inspection system 100 known in the art such as, but not limited to, particle-based or optical inspection systems.

Further, defects in a sample die may be characterized by comparing a voltage contrast image of the sample die with a voltage contrast image of a reference die (e.g., die-to-die (D2D) inspection, standard reference die (SRD) inspection, or the like) or by comparing a voltage contrast image of the sample die with an image based on design characteristics (e.g., die-to-database (D2DB) inspection). Inspection systems using persistent data (e.g., stored data) is generally described in U.S. Pat. No. 8,126,255, issued on Feb. 28, 2012, which is incorporated herein by reference in its entirety. Inspection systems using design data of a sample to facilitate inspection is generally described in U.S. Pat. No. 7,676,077, issued on Mar. 9, 2010, and U.S. Pat. No. 6,154,714, issued on Nov. 28, 2000, and U.S. Pat. No. 8,041,103, issued on Oct. 18, 2011, which are incorporated herein by reference in their entirety. The determination of defect and fault sources are generally described in U.S. Pat. No. 6,920,596, issued on Jul. 19, 2005, U.S. Pat. No. 8,194,968, issued on Jun. 5, 2015, and U.S. Pat. No. 6,995,393, issued on Feb. 7, 2006, which are incorporated herein by reference in their entirety. Device property extraction and monitoring is generally described in U.S. Pat. No. 8,611,639, issued on Dec. 17, 2013. Sample device designs suitable for VCI are generally described in U.S. Pat. No. 6,509,197, issued on Jan. 21, 2003, U.S. Pat. No. 6,528,818, issued on Mar. 4, 2003, U.S. Pat. No. 6,576,923, issued on Jun. 10, 2003, and U.S. Pat. No. 6,636,064, issued on Oct. 21, 2003, which are incorporated herein by reference in their entirety. The use of reticles in inspection systems is generally described in U.S. Pat. No. 6,529,621, issued on Mar. 4, 2003, U.S. Pat. No. 6,748,103, issued on Jun. 8, 2004, and U.S. Pat. No. 6,966,047, issued on Nov. 15, 2005, which are incorporated herein by reference in their entirety. Generating an inspection process or inspection target is generally described in U.S. Pat. No. 6,691,052, issued on Feb. 10, 2004, U.S. Pat. No. 6,921,672, issued on Jul. 26, 2005, and U.S. Pat. No. 8,112,241, issued on Feb. 7, 2012, which are incorporated herein by reference in their entirety. Determination of critical areas of semiconductor design data is generally described in U.S. Pat. No. 6,948,141, issued on Sep. 20, 2005, which is incorporated by reference herein in its entirety.

The use of dual-energy electron flooding for neutralization of a charged substrate is generally described in U.S. Pat. No. 6,930,309, issued on Aug. 16, 2005, which is incorporated herein by reference in its entirety. The use of particle beams with different energies are generally described in U.S. Pat. No. 6,803,571, issued on Oct. 12, 2004, and U.S. Pat. No. 7,217,924, issued on May 15, 2007, which are incorporated herein by reference in their entirety. The use of multiple particle beams for sample inspection are generally described in U.S. Pat. No. 6,774,646, issued on Aug. 10, 2004, U.S. Pat. No. 7,391,033, issued on Jun. 24, 2008, and U.S. Pat. No. 8,362,425, issued on Jan. 29, 2013, which are incorporated herein by reference in their entirety. Multiple-column particle beam systems and methods are generally described in U.S. Pat. No. 8,455,838, issued on Jun. 4, 2013, which is incorporated herein by reference in its entirety.

Figure 10A:
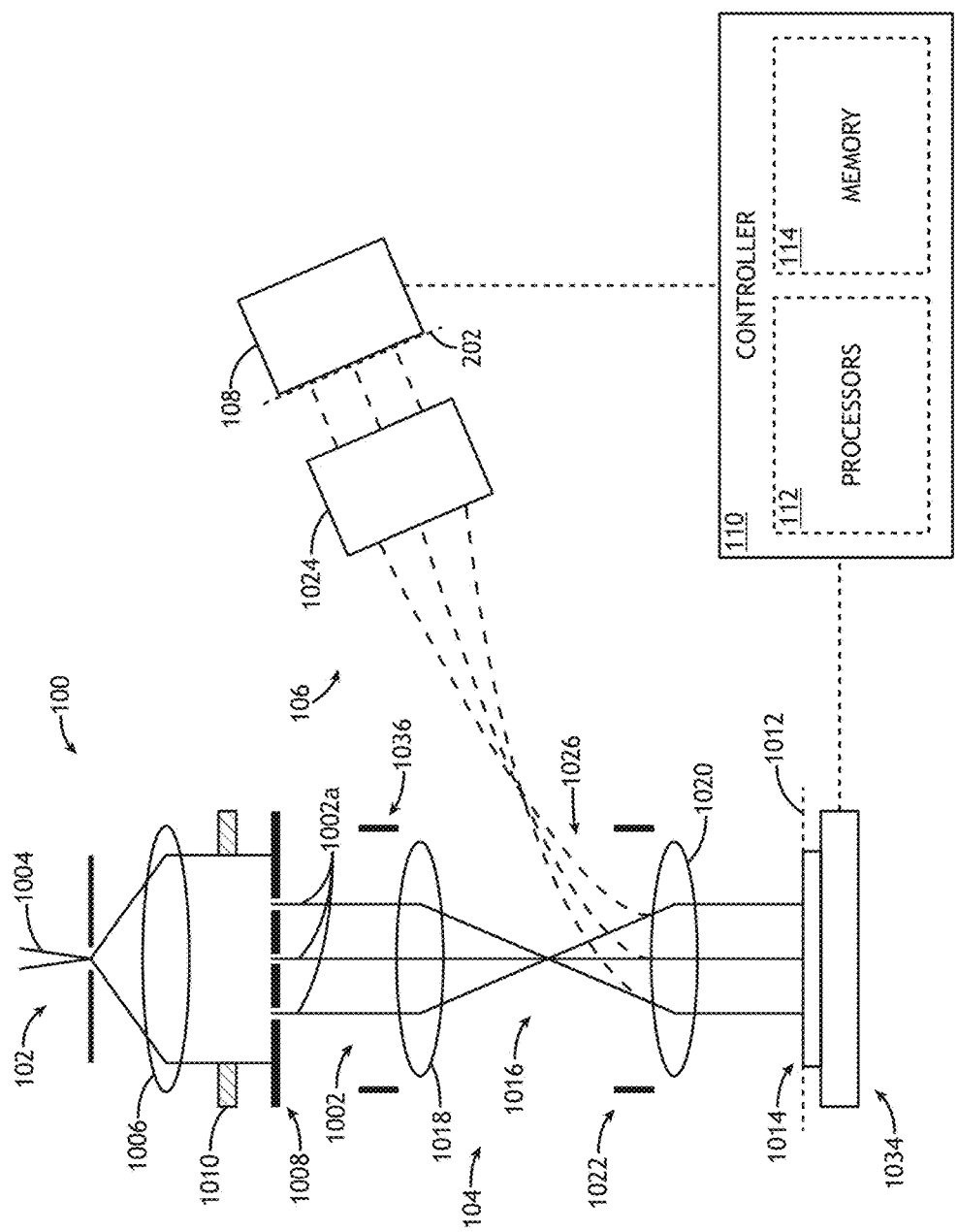
FIG. 10A is a conceptual view of a particle-based multi-beam inspection system, in accordance with one or more embodiments of the present disclosure.

FIG. 10A is a conceptual view of a particle-based multi-beam inspection system 100, in accordance with one or more embodiments of the present disclosure. In one embodiment, the multi-beam illumination source 102 generates a beam array 1002 including two or more illumination beams 1002a. The multi-beam illumination source 102 may include any type of particle source known in the art suitable for generating illumination beams 1002a including any type of particles. For example, the multi-beam illumination source 102 may include an electron source such that one or more illumination beams 1002a include electron beams. By way of another example, the multi-beam illumination source 102 may include an ion source such that the one or more illumination beams 1002a may include ion beams. Further, the multi-beam illumination source 102 may include, but is not limited to, one or more electron guns, one or more ion guns, one or more cathode sources, one or more emitter tips, one or more anodes, or one or more gate valves suitable for generating particle radiation.

As described previously herein, the multi-beam illumination source 102 may include one or more additional illumination sources (e.g., optical sources, or the like) suitable for illuminating a sample for the purposes of sample inspection and/or sample alignment. For example, the multi-beam illumination source 102 may generate electromagnetic radiation having any wavelength including, but not limited to X-rays, visible light (e.g., ultraviolet (UV) wavelengths, visible wavelengths, infrared (IR) wavelengths, and the like). Further, the illumination beams 1002a may exhibit any selected degree of spatial or temporal coherence.

The multi-beam illumination source 102 may generate the beam array 1002 using any method known in the art. In one embodiment, as illustrated in FIG. 10A, the multi-beam illumination source 102 may include an emission source 1004 and a gun lens 1006 to collect particles emitted from the emission source 1004 and direct them to a beam lens array 1008. For example, the beam lens array 1008 may include a series of apertures and/or lenses arranged to split the particles from the gun lens 1006 into the array of illumination beams 1002a. The multi-beam illumination source 102 may further include a current-control aperture 1010 (e.g., a current-control aperture) to limit the size and/or current of particles directed to the beam lens array 1008. In one embodiment, the current-control aperture 1010 may control the spatial extent of particles incident on the beam lens array 1008 and may thus control the number of illumination beams 1002a in the beam array 1002.

In another embodiment, though not shown, one or more of the illumination beams 1002a may be generated by a separate emission source 1004 the multi-beam illumination source 102 may two or more emission sources 1004 to generate the illumination beams 1002a of the beam array 1002.

The illumination sub-system 104 may include any number of focusing elements and/or beam-shaping elements to direct the beam array 1002 to a sample plane 1012 at which a sample 1014 is located. In this regard, the array of locations in the sample plane 1012 represent an array of measurement locations (e.g., on the sample 1014) interrogated by the multi-beam inspection system 100.

In one embodiment, the illumination sub-system 104 includes one or more illumination sub-system focusing elements 1016 (e.g., lenses). For example, as illustrated in FIG. 10A, the illumination sub-system focusing elements 1016 may include a transfer lens 1018 and an objective lens 1020 forming a compound system to direct the beam array 1002 to the sample plane 1012 (e.g., to the sample 1014). In one instance, the illumination sub-system focusing elements 1016 image the beam lens array 1008 to the sample plane 1012. In another instance (not shown), the beam lens array 1008 focuses each illumination beam 1002a to a virtual source plane, and the illumination sub-system focusing elements 1016 then image the virtual source plane on the sample 1014. Such a configuration may facilitate additional control over the focal properties of the illumination beams 1002a.

In another embodiment, the illumination sub-system 104 includes beam-shaping elements to further modify the characteristics of the illumination beams 1002a. For example, the illumination sub-system 104 may include aberration-correcting components such as, but not limited to, stigmators for mitigating astigmatism.

Accordingly, the illumination sub-system 104 may be selected and/or adjusted to provide selected focal characteristics of the illumination beams 1002a on the sample 1014. For example, the spacing between illumination beams 1002a may be adjusted based on a magnification of the illumination sub-system focusing elements 1016. By way of another example, the numerical aperture of the illumination beams 1002a may be adjusted based on the focal powers of the illumination sub-system focusing elements 1016.

Further, the illumination sub-system focusing elements 1016 may include any type of lenses known in the art including, but not limited to, electrostatic, magnetic, uni-potential, or double-potential lenses. Additionally, the illumination sub-system 104 may include one or more elements held at a controlled electrical potential with respect to the sample 1014 to modify the landing energies of the illumination beams 1002a.

The imaging sub-system 106 may include any number of focusing elements and/or beam-shaping elements to image the array of measurement spots to a detection plane 202 for detection with the detection assembly 108. In one embodiment, the imaging sub-system 106 includes one or more particle lenses (e.g., electrostatic, magnetic, uni-potential, double potential lenses, or the like) to capture and image particles such as, but not limited to secondary electrons or backscattered electrons from the sample 1014 in response to the illumination beams 1002a. In another embodiment, the imaging sub-system 106 includes one or more optical lenses to capture and image electromagnetic radiation emanating from the sample 1014 in response to the illumination beams 1002a.

In one embodiment, as illustrated in FIG. 10A, the imaging sub-system 106 includes a Wien filter 1022 to separate particles (e.g., electrons) emanating from the sample 1014 from the illumination beams 1002a. For example, the Wien filter 1022 may be located above the objective lens 1020 to redirect particles collected by the objective lens 1020 towards the detection assembly 108. Further, the imaging sub-system 106 may include one or more imaging sub-system focusing elements 1024 to image the array of measurement locations onto the detection plane 202.

In another embodiment, though not shown, the imaging sub-system 106 includes a secondary electron bender to further deflect particles redirected by the Wien filter 1022. For example, a secondary electron bender may include, but is not required to include, charged plates with different applied voltages through which collected electrons propagate. In this regard, the secondary electron bender may facilitate the inclusion of the adjustable beam-control elements 1026.

In another embodiment, the imaging sub-system 106 includes one or more adjustable beam-control elements 1026 suitable for modifying the positions of one or more imaged spots 204 in the detection plane 202 based on feedback signals. For example, the adjustable beam-control elements

1026 may receive feedback signals from the detection assembly 108 (e.g., the position detectors 118 of the detection assembly 108) indicating a misalignment of one or more detection elements 116. In response, the adjustable beam-control elements 1026 may selectively modify positions of the relevant imaged spots 204 to maintain alignment of the detection elements 116.

Figure 10B:
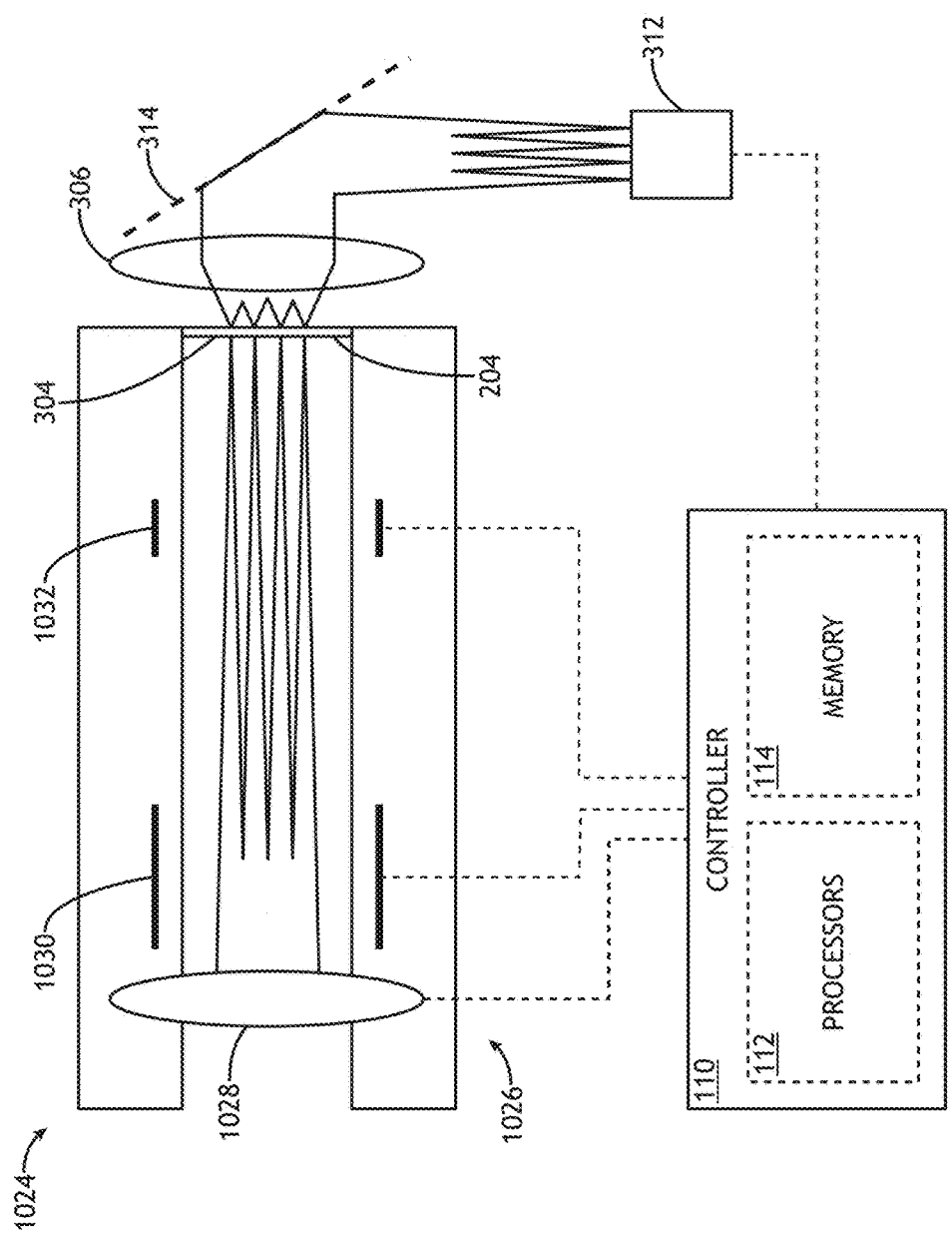
FIG. 10B is a conceptual view of adjustable beam-control elements suitable for modifying the positions of one or more imaged spots in the detection plane, in accordance with one or more embodiments of the present disclosure.

FIG. 10B is a conceptual view of adjustable beam-control elements 1026 suitable for modifying the positions of one or more imaged spots 204 in the detection plane 202, in accordance with one or more embodiments of the present disclosure. In one embodiment, the adjustable beam-control elements 1026 include one or more adjustable focusing elements 1028 having an adjustable focal power and/or rotation adjustment. For example, the adjustable focusing elements 1028 may adjust the magnification of the imaged spots 204 and thus the size and spacing between the imaged spots 204. In another embodiment, the adjustable beam-control elements 1026 include one or more deflectors 1030 configured to deflect the imaged spots 204 in one or more selected directions. For example, the adjustable beam-control elements 1026 may include two deflectors 1030 configured to deflect the imaged spots 204 along orthogonal directions. In another embodiment, the adjustable beam-control elements 1026 includes one or more stigmators 1032 suitable for introducing and/or mitigating aberrations such as astigmatism into the imaged spots 204. In another embodiment, the adjustable beam-control elements 1026 provide near-edge correction as a means of adjusting positions of one or more imaged spots 204. For example, the stigmators 1032 may uniformly modify the imaged spots 204.

The multi-beam inspection system 100 may generate an extended image of the sample 1014 based on scanning the sample 1014 and/or the beam array 1002 and generating a composite image based on signals received from the detection assembly 108. In one embodiment, the multi-beam inspection system 100 includes a sample stage 1034 to secure and translate the sample 1014. The sample stage 1034 may include any device suitable for positioning and/or scanning the sample 1014 within the multi-beam inspection system 100. For example, the sample stage 1034 may include any combination of linear translation stages, rotational stages, tip/tilt stages, or the like.

In another embodiment, the multi-beam inspection system 100 includes one or more particle scanning elements 1036. The particle scanning elements 1036 may include, but are not limited to, one or more scanning coils or deflectors suitable for controlling a position of the illumination beams 1002*a* relative to the surface of the sample 1014. In this regard, particle scanning elements 1036 may scan the illumination beams 1002*a* across the sample 1014 in a selected pattern. It is noted herein that the multi-beam inspection system 100 may operate in any scanning mode known in the art. For example, the multi-beam inspection system 100 may operate in a step-and-scan mode when scanning the illumination beams 1002*a* across the surface of the sample 1014. In this regard, the multi-beam inspection system 100 may scan an illumination beam 1002*a* across the sample 1014, which may be nominally stationary with respect to the illumination beam 1002*a* or in synchronous motion with the illumination beam 1002*a*.

Further, the multi-beam illumination source 102 may generate a beam array 1002 having any selected number of illumination beams 1002*a* with any distribution for illuminating the sample 1014. For example, the multi-beam inspection system 100 may illuminate a sample 1014 with a 1-D array (e.g., a line array) of illumination beams 1002*a* distributed along a first direction to generate a line image and may further translate the sample 1014 mounted on a sample stage 1034 along an orthogonal direction to generate a line-scan image of any desired length. By way of another example, the multi-beam inspection system 100 may illuminate the sample 1014 with a 2D array of illumination beams 1002*a* and may translate the sample 1014 and/or the beam array 1002 in a coordinated pattern to generate an image of the sample 1014.

Figure 11:
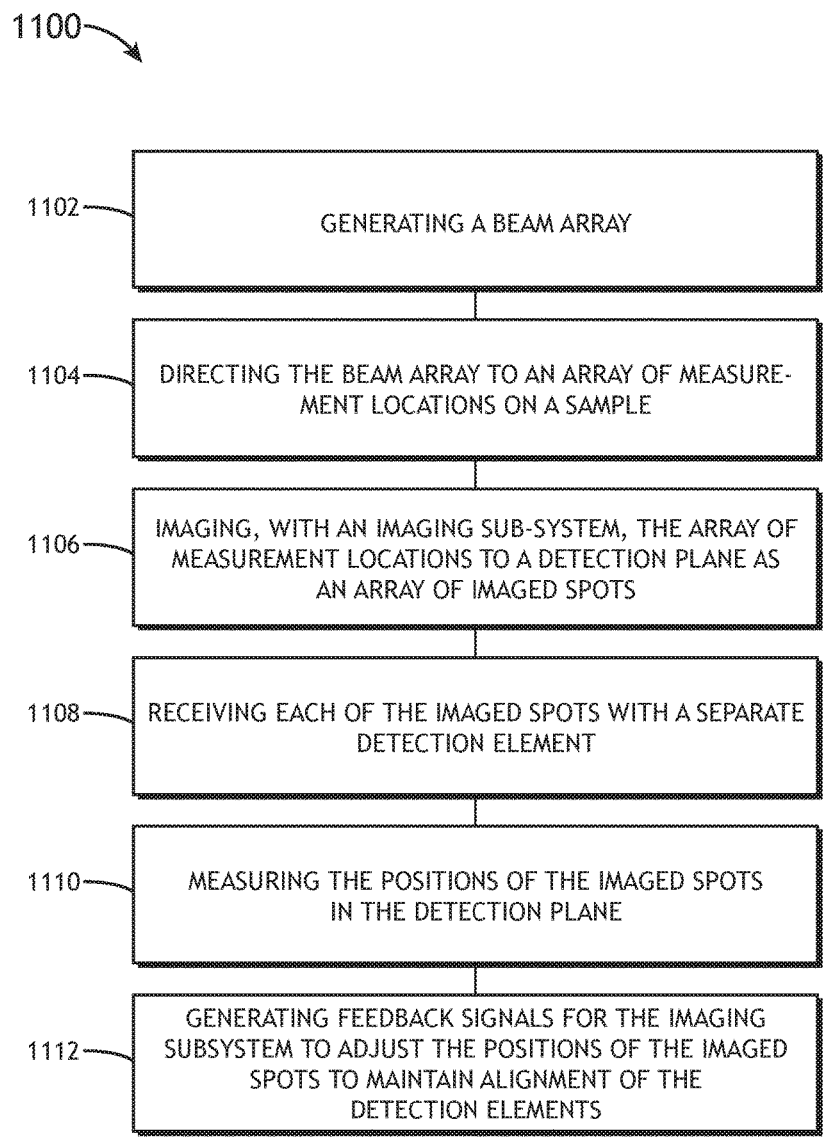
FIG. 11 is a flow diagram illustrating steps performed in a method for simultaneously detecting positions of multiple particle beams, in accordance with one or more embodiments of the present disclosure.

FIG. 11 is a flow diagram illustrating steps performed in a method 1100 for simultaneously detecting positions of multiple particle beams, in accordance with one or more embodiments of the present disclosure. Applicant notes that the embodiments and enabling technologies described previously herein in the context of the multi-beam inspection system 100 should be interpreted to extend to method 1100. It is further noted, however, that the method 1100 is not limited to the architecture of the multi-beam inspection system 100.

In one embodiment, the method 1100 includes a step 1102 of generating a particle beam array with an illumination source. The particle beam may include any type of particles such as, but not limited to, electrons, ions, or neutral particles. In another embodiment, the method 1100 includes a step 1104 of directing the particle beam array to an array of measurement locations on a sample with an illumination sub-system. In another embodiment, the method 1100 includes a step 1106 of imaging the array of measurement locations to an array of imaged spots at a detection plane with an imaging sub-system. For example, the imaging sub-system may collect particles emanating from the sample in response to the particle beam array such as, but not limited to, secondary electrons or backscattered electrons.

In another embodiment, the method 1100 includes a step 1108 of receiving the imaged spots with separate detection elements of an array of detection elements. For example, a detection assembly may include an array of detection elements suitable for generating a separate detection signal channel for each received imaged spot. In another embodiment, the method 1100 includes a step 1110 of measuring, with one or more position detectors, positions of the imaged spots at the detection plane. For example, the detection assembly may further include position detectors configured to measure and continually monitor the positions of the imaged spots at the detection plane. Further, the position detectors may be calibrated to the array of detection elements such that the position detectors may monitor the accuracy of the alignment of the imaged spots on the array of detection elements.

Simultaneous detection of the intensities of the imaged spots and the positions of the imaged spots on the array of detection elements may be achieved in various ways. In one embodiment, a scintillator is located at the detection plane to absorb the particles from the sample (e.g., associated with the imaged spots) and subsequently emit electromagnetic radiation (e.g., light) in response. Further, the detection plane (and thus the light from the scintillator associated with the imaged spots) may be re-imaged to two conjugate secondary image planes. In this regard, the detection elements may be located at one of the conjugate secondary image planes and a position detector (e.g., a camera) may be located at the other conjugate secondary image plane. Accordingly, deviations of the positions of the imaged spots at the detection plane result in simultaneous modifications of the secondary image on both the detection elements and the position detector.

Additionally, the array of detection elements may be coupled to an optical fiber bundle. In this regard, the input faces of the fiber bundle may be located at one of the conjugate secondary image planes and may be further arranged as a scaled version of the array of imaged spots. Accordingly, the secondary images of the detection plane may be adjusted such that secondary images of the imaged spots are each collected by a different optical fiber.

In another embodiment, an array of multi-pixel detection elements that are directly sensitive to particles from the sample may be located at the detection plane and arranged as a scaled version of the array of imaged spots such that each imaged spot is captured by a separate multi-pixel detection element. The positions of the imaged spots on a multi-pixel detection element may be determined based on the energies absorbed by each pixel relative to the aggregate energy absorbed by the entire multi-pixel detection element.

In another embodiment, the method 1100 includes a step 1112 of generating feedback signals for the imaging sub-system based on the measured positions of the imaged spots to adjust the positions of the one or imaged spots in the detection plane to maintain alignment of the array of detection elements. For example, the imaging sub-system may include adjustable beam control elements such as, but not limited to, adjustable lenses, deflectors, stigmators, or the like suitable for modifying the positions of the imaged spots at the detection plane. Accordingly, the imaging sub-system may continually adjust the positions of the imaged spots at the detection plane to maintain alignment of the detection elements.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected" or "coupled" to each other to achieve the desired functionality, and any two components capable of being so associated can also be viewed as being "couplable" to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A multi-beam metrology system, comprising:
   an illumination source configured to generate a beam array;
   an illumination sub-system including one or more focusing elements configured to direct the beam array to a sample at an array of measurement locations;
   an imaging sub-system configured to image the array of measurement locations as an array of imaged spots in a detection plane, the imaging sub-system including at least one of an adjustable lens, an adjustable deflector, or an adjustable stigmator, the one or more adjustable beam control elements configured to adjust positions of one or more of the imaged spots in the detection plane; and
   a detection assembly configured to generate detection signal channels associated with at least some of the imaged spots, the detection assembly comprising:
      an array of detection elements configured to receive the imaged spots with separate detection elements; and
      one or more position detectors configured to measure positions of the imaged spots in the detection plane, wherein the detection assembly generates feedback signals indicative of alignment of the imaged spots on the array of detection elements based on the positions of the imaged spots in the detection plane, wherein the imaging sub-system adjusts the positions of one or more of the imaged spots in the detection plane based on the feedback signals to maintain alignment of the imaged spots on the array of detection elements.

2. The multi-beam metrology system of claim 1, wherein the illumination source comprises:
   one or more particle beam sources, wherein the beam array includes a particle beam array.

3. The multi-beam metrology system of claim 2, wherein the particle beam array comprises:
   an array of at least one of electron beams or ion beams.

4. The multi-beam metrology system of claim 2, wherein the detection assembly comprises:
   a scintillator located at the detection plane, the scintillator configured to generate optical radiation in response to receiving particles associated with the imaged spots; and
   one or more detector lenses configured to image the optical radiation generated by the scintillator onto the array of detection elements.

5. The multi-beam metrology system of claim 4, wherein the array of detection elements comprises:
   an array of optical fibers, wherein the one or more detector lenses provide an image of the optical radiation generated by the scintillator to input faces of the array of optical fibers; and
   one or more optical detectors coupled to output faces of the array of optical fibers and configured to receive the optical radiation generated by the scintillator and propagating through the array of optical fibers.

6. The multi-beam metrology system of claim 5, wherein the detection assembly further comprises:
   a beamsplitter located between the one or more detector lenses and the one or more position detectors configured to provide a secondary image of the optical radiation generated by the scintillator to the one or more position detectors, wherein the feedback signals maintain alignment of the imaged spots on the input faces of the array of optical fibers based on the secondary image.

7. The multi-beam metrology system of claim 6, wherein the one or more position detectors comprises:
   a camera.

8. The multi-beam metrology system of claim 7, wherein the camera comprises:
   at least one of a charge-coupled device or a complementary metal oxide semiconductor device.

9. The multi-beam metrology system of claim 1, wherein the array of detection elements comprises:
   an array of diodes located at the detection plane.

10. The multi-beam metrology system of claim 9, wherein a diode of the array of diodes includes two or more pixels, wherein the one or more position detectors includes the two or more pixels, wherein a position of an imaged spot of the array of imaged spots on the diode is determined based on a relative signal strength of the two or more pixels, wherein the feedback signals maintain alignment of the imaged spots on the array of diodes.

11. The multi-beam metrology system of claim 10, wherein the two or more pixels comprises:
   three pixels.

12. The multi-beam metrology system of claim 9, wherein the array of diodes comprises:
   an array of PIN diodes.

13. The multi-beam metrology system of claim 1, wherein the imaging sub-system is configured to adjust a focal position of at least one imaged spot with respect to the detection plane based on the feedback signals.

14. The multi-beam metrology system of claim 1, wherein the imaging sub-system is configured to adjust a transverse position of at least one imaged spot in the detection plane based on the feedback signals.

15. The multi-beam metrology system of claim 1, wherein the imaging sub-system is configured to provide at least one of astigmatism correction or near-edge correction based on the feedback signals.

16. A detection assembly, comprising:
   an array of detection elements configured to receive one or more imaged spots at a detection plane with separate detection elements, wherein the one or more imaged spots include radiation emanating from a sample in response to a beam array from a multi-beam illumination source and imaged to the detection plane by an imaging sub-system, wherein the imaging sub-system includes at least one of an adjustable lens, an adjustable deflector, or an adjustable stigmator; and
   one or more position detectors configured to measure positions of the imaged spots in the detection plane, wherein the detection assembly generates feedback signals indicative of alignment of the imaged spots on the array of detection elements based on the positions of the imaged spots in the detection plane, wherein the imaging sub-system adjusts the positions of one or more of the imaged spots in the detection plane based on the feedback signals to maintain alignment of the imaged spots on the array of detection elements.

17. The detection assembly of claim 16, wherein the beam array comprises:
   an array of at least one of electron beams or ion beams.

18. The detection assembly of claim 16, wherein the detection assembly further comprises:
   a scintillator located at the detection plane, the scintillator configured to generate optical radiation in response to receiving particles associated with the imaged spots; and
   one or more detector lenses configured to image the optical radiation generated by the scintillator onto the array of detection elements.

19. The detection assembly of claim 18, wherein the array of detection elements comprises:
   an array of optical fibers, wherein the one or more detector lenses provide an image of the optical radiation generated by the scintillator to input faces of the array of optical fibers; and
   one or more optical detectors coupled to output faces of the array of optical fibers and configured to receive the optical radiation generated by the scintillator and propagating through the array of optical fibers.

20. The detection assembly of claim 19, wherein the detection assembly further comprises:
   a beamsplitter located between the one or more detector lenses and the one or more position detectors configured to provide a secondary image of the optical radiation generated by the scintillator to the one or more position detectors, wherein the feedback signals maintain alignment of the imaged spots on the input faces of the array of optical fibers based on the secondary image.

21. The detection assembly of claim 20, wherein the one or more position detectors comprises:
   a camera.

22. The detection assembly of claim 21, wherein the camera comprises:
   at least one of a charge-coupled device or a complementary metal oxide semiconductor device.

23. The detection assembly of claim 16, wherein the array of detection elements comprises:
   an array of diodes located at the detection plane.

24. The detection assembly of claim 23, wherein a diode of the array of diodes includes two or more pixels, wherein the one or more position detectors includes the two or more pixels, wherein a position of an imaged spot of the array of imaged spots on the diode is determined based on a relative signal strength of the two or more pixels, wherein the feedback signals maintain alignment of the imaged spots on the array of diodes.

25. The detection assembly of claim 24, wherein the two or more pixels comprises:
   three pixels.

26. The detection assembly of claim 23, wherein the array of diodes comprises:
   an array of PIN diodes.

27. The detection assembly of claim 16, wherein the imaging sub-system is configured to adjust a focal position of at least one imaged spot with respect to the detection plane based on the feedback signals.

28. The detection assembly of claim 16, wherein the imaging sub-system is configured to adjust a transverse position of at least one imaged spot in the detection plane based on the feedback signals.

29. The detection assembly of claim 16, wherein the imaging sub-system is configured to provide at least one of astigmatism correction or near-edge correction based on the feedback signals.

30. A method for detecting positions of multiple particle beams, comprising:
   generating a particle beam array with an illumination source;
   directing the particle beam array to an array of measurement locations on a sample;
   imaging the array of measurement locations to an array of imaged spots at a detection plane with an imaging sub-system including at least one of an adjustable lens, an adjustable deflector, or an adjustable stigmator;
   receiving the imaged spots with separate detection elements of an array of detection elements;

measuring, with one or more position detectors, positions of the imaged spots at the detection plane; and generating feedback signals for the imaging sub-system based on the measured positions of the imaged spots to adjust the positions of the one or imaged spots in the detection plane to maintain alignment of the imaged spots on the array of detection elements.

31. The method of claim 30, further comprising:

adjusting the positions of the imaged spots in the detection plane with the imaging sub-system based on the feedback signals to maintain alignment of the array of detection elements.

\* \* \* \* \*